United States Patent [19]

Blum et al.

[11] Patent Number: 4,908,138

[45] Date of Patent: Mar. 13, 1990

[54] HYDROXYACETONITRILE DIPHOSPHONIC ACID, A PROCESS FOR ITS PRODUCTION, AND ITS USE

[75] Inventors: Helmut Blum, Duesseldorf; Siglinde Hemmann, Meerbusch, both of Fed. Rep. of Germany

[73] Assignee: Henkel Kommanditgesellschaft auf Aktien, Duesseldorf, Fed. Rep. of Germany

[21] Appl. No.: 223,210

[22] Filed: Jul. 22, 1988

[30] Foreign Application Priority Data

Jul. 25, 1987 [DE] Fed. Rep. of Germany ....... 3724654

[51] Int. Cl.$^4$ .................. C07C 120/00; C07C 121/36; C07C 121/34; C02F 5/14
[52] U.S. Cl. .................... 210/700; 558/312; 558/315; 558/386
[58] Field of Search ............ 558/312, 315, 386; 210/700

[56] References Cited

U.S. PATENT DOCUMENTS

| | | | |
|---|---|---|---|
| 2,026,078 | 12/1935 | Walker | 294/49 |
| 3,488,419 | 1/1970 | McCune et al. | 424/49 |
| 3,617,576 | 11/1971 | Kerst | 558/386 X |
| 3,629,326 | 12/1971 | Frank et al. | 558/386 X |
| 3,846,420 | 11/1974 | Wollmann et al. | 260/247 |
| 3,962,432 | 6/1976 | Schmidt-Duenker | 424/204 |
| 4,054,598 | 10/1977 | Blum et al. | 260/502.5 |
| 4,134,969 | 1/1979 | Schmidt-Duenker | 424/49 |
| 4,239,695 | 12/1980 | Chai et al. | 558/386 X |
| 4,370,280 | 1/1983 | Oediger et al. | 558/386 X |
| 4,440,646 | 4/1984 | Budnick | 210/699 |
| 4,645,762 | 2/1987 | Biere et al. | 514/108 |

FOREIGN PATENT DOCUMENTS

1002355 2/1957 Fed. Rep. of Germany .
2625767 12/1977 Fed. Rep. of Germany .

OTHER PUBLICATIONS

Zeitschrift Für Naturforschung B (Chemical Sciences) vol. 43, No. 1, Jan. 1988, pp. 75–81.

*Primary Examiner*—Joseph Paul Brust
*Attorney, Agent, or Firm*—Ernest G. Szoke; Wayne C. Jaeschke; Henry E. Millson, Jr.

[57] ABSTRACT

Hydroxyacetonitrile diphosphonic acid corresponding to the following general formula

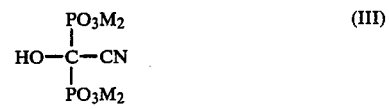

(III)

in which M represents H or a cation of a base, and salts thereof; to a process for their preparation comprising reacting 3-R$^1$-3-oxo-1-aminopropane-1,1-diphosphonic acids corresponding to the following general formula

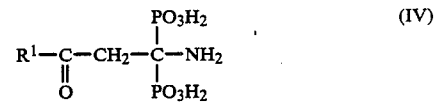

(IV)

in which R$^1$ is a tertiary substituted alkyl group, an optionally substituted cycloalkyl group or an optionally substituted aryl or heteroaryl radical, with nitrous acid, the secondary product R$^1$-COOH and unreacted starting material are separated off from the reaction mixture and the hydroxyacetonitrile diphosphonic acid is obtained in the form of a salt by addition of a base; and to the use of the above compounds as complexing agents and as thresholders.

23 Claims, No Drawings

HYDROXYACETONITRILE DIPHOSPHONIC ACID, A PROCESS FOR ITS PRODUCTION, AND ITS USE

BACKGROUND OF THE INVENTION

1. Field of the Invention

This invention relates to hydroxyacetonitrile disphosphonic acid and its salts, to a process for their production, and to their use as thresholders or as complexing agents.

2. Statement of Related Art

1-Amino-1,1-diphosphonic acids corresponding to the following general formula

in which A, B and C represent aliphatic, cycloaliphatic or aromatic hydrocarbon radicals, in addition to which B and C can also represent a hydrogen atom, are known from the prior art. They are prepared by reaction of nitriles with phosphorus trihalides and subsequent hydrolysis or alcoholysis (German application 10 02 355), reaction of nitriles with phosphorous acid (German application 26 25 767) or reaction of carboxylic acid amides with phosphorus trihalides in the presence of phosphorous acid and subsequent hydrolysis (German application 19 58 123). Phosphonic acids corresponding to general formula (I) above have the ability to complex heavy metal ions and alkaline earth metal ions. Accordingly, they are widely used as complexing agents or chelating agents in the softening of water, in detergent manufacture, in the textile field and in papermaking.

It is known from German application 16 17 729 that 1-hydroxyethane-1,1-diphosphonic acid can be used as a complexing agent for inhibiting the formation of tartar.

U.S. Pat. No. 3,686,290 describes the synthesis of ethylene-1,1-diphosphonic acid and its use as a complexing agent for heavy metal ions.

In addition, structurally related compounds corresponding to the following general formula

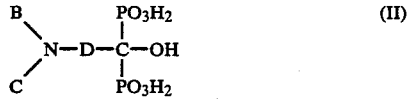

are known as complexing agents. In formula (II), B and C represent hydrogen or aliphatic or aromatic radicals in analogy to general formula (I) above, while D is a $C_1$–$C_5$ alkylene radical. German application 34 34 667 and German patent 25 34 391 describe the use of compounds corresponding to general formula (II) and water-soluble salts thereof as complexing agents for alkaline earth metal ions, preferably calcium ions, and as thresholders. German patent 24 05 254 describes the use of the above compounds in the prophylaxis and treatment of disorders of the calcium or phosphate metabolism in the human and animal body.

DESCRIPTION OF THE INVENTION

It has now surprisingly been found that a new compound and salts thereof can be obtained by reaction of 3-$R^1$-3-oxo-1-aminopropane-1,1-diphosphonic acids with nitrous acid and that these compounds show favorable complexing properties and can therefore be used as thresholders in compositions, for example, for inhibiting calcite scaling.

In addition, the compounds of the invention are particularly effective tartar inhibitors and are capable on the one hand of inhibiting the formation of tartar and, on the other hand, of highly stabilizing the dental enamel, thus making it difficult for polysugars to attack hydroxyl apatite, the basic substance of teeth.

The present invention relates to hydroxyacetonitrile diphosphonic acid and its salts corresponding to the following general formula

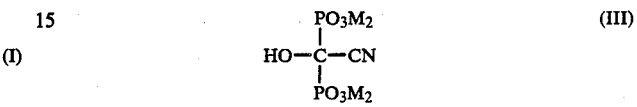

in which M represents H or the cation of a base, i.e., salts thereof.

The invention also relates to a process for the preparation of compounds of formula (III) above, in which M represents H or the cation of a base, wherein a 3-$R^1$-3-oxo-1-aminopropane-1,1-diphosphonic acid corresponding to the following general formula

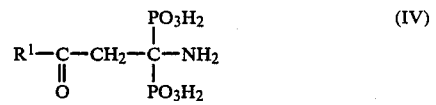

in which $R^1$ represents a tertiary alkyl group having the general formula —($R^2$)C($R^3$)($R^4$), where $R^2$ and $R^3$ independently of one another represent a $C_1$–$C_3$ alkyl group, and $R_4$ represents a $C_1$–$C_{10}$ alkyl group, an optionally substituted cycloalkyl group, or an aryl or heteroaryl group optionally substituted by halogen, $C_1$–$C_5$ alkoxy, di-$C_1$–$C_5$-alkyl, is reacted with nitrous acid, which has preferably been prepared in situ from an aqueous alkali metal nitrite solution and dilute mineral acid, the molar ratio of nitrous acid or alkali metal nitrite to the compound of formula (IV) being in the range of from 1:1 to 6:1, at a temperature in the range of from room temperature (20° C.) to 75° C. The resulting reaction mixture is then worked up to obtain the compound of formula (III). The compound of formula (III), in which M represents H, can be isolated from the reaction mixture by careful working up using an acidic reagent. The reaction product corresponding to formula (III), in which M represents H, is then optionally converted by addition of basic reagents corresponding to the formula $M^+OH^-$, where $M^+$ is an alkali metal or ammonium cation $R^5R^6R^7R^8N^+$, in which $R^5$, $R^6$, $R^7$ and $R^8$ independently of one another are hydrogen or a branched or unbranched $C_1$–$C_{12}$ alkyl radical, into compounds corresponding to formula (III) in which M is an alkali metal or ammonium cation as defined above. These compounds are then isolated and purified.

The present invention also relates to the use of the compounds of formula (III) as complexing agents and as thresholders.

The new compounds of formula (III) according to the invention can be called hydroxyacetonitrile diphosphonic acid or salts thereof, depending on the substituent M.

Compounds of formula (III) above in which M—instead of the proton for the free acid—can also represent a cation of a water-soluble base, particularly alkali metal cations or an ammonium cation having the general formula $R^5R^6R^7R^8N^+$, have a complexing effect and, accordingly, are a preferred subject of the invention. A major advantage of these salts derived from the free acid is that they clearly improve the solubility in water of the compound of formula (III) in which M represents H. The usefulness of such compounds in preparations having a threshold effect is thus also improved. According to the invention, such cations as $Na^+$, or $K^+$ are particularly suitable alkali metal cations. However, M can also represent ammonium cations corresponding to the above general formula, in which $R^5$, $R^6$, $R^7$ and $R^8$ independently of one another are hydrogen or branched or unbranched $C_1$–$C_{12}$ alkyl radicals. Accordingly, alkyl radicals include methyl, ethyl, and any branched or unbranched propyl, butyl, pentyl, hexyl, heptyl, octyl, nonyl, decyl, undecyl or dodecyl. Also, partial salts in which one to three M groups are hydrogen and the remaining M groups are alkali metal or ammonium cations are also within the scope of the invention.

According to the invention, preferred water-soluble salts are alkali metal salts of formula (III) in which M represents an alkali metal cation. The sodium salts are particularly preferred.

As described above, the present invention also relates to a process for the production of compounds of formula (III) by reaction of 3-$R^1$-3-oxo-1-aminopropane-1,1-diphosphonic acids with nitrous acid. On the one hand, it is entirely plausible to those skilled in the art that, in the same way as a primary aromatic amine, a primary aliphatic amine stabilized by phosphonic acid groups in the 1-position should not remain at the diazonium salt stage in the reaction with dilute nitrous acid, particularly at elevated temperature, but would be immediately "boiled down" to the hydroxy compound. This was also demnstrated for the corresponding 1-aminoalkane-1,1-diphosphonic acids by K. H. Worms and H. Blum, Z. anorg. allg. Chem. (1979) 457, 214. However, it is quite surprising and unexpected that, in addition, oxidative cleavage occurs between the keto group and the methylene group in the starting molecule, and that compounds according to the invention containing a cyano group in the molecule, in addition to the secondary product $R^1$-COOH, can be isolated from the reaction mixture.

Accordingly, this process must be regarded as chemically unique because the formation of a cyano group under these reaction conditions was not foreseeable.

In the compounds of formula (IV) $R^1$ can represent a tertiary alkyl group having the general formula —$(R^2)C(R^3)(R^4)$, in which $R^2$ and $R^3$ independently of one another represent a $C_1$–$C_3$ alkyl group and $R^4$ represents a $C_1$–$C_{10}$ alkyl group. $R^2$ and $R^3$ independently of one another can represent methyl, ethyl or propyl, preferably methyl or ethyl. $R^4$ can represent a linear or branched $C_1$–$C_{10}$ alkyl group, such as methyl, ethyl, propyl, butyl, pentyl, hexyl, heptyl, octyl, nonyl, or decyl, and branched isomers thereof.

$R^1$ can also be an optionally methyl or ethyl substituted $C_3$–$C_6$ cycloalkyl group. If a methyl or ethyl substituent is present, it is preferably present in the 1-position of the cycloalkyl group. Cycloalkyl groups include cyclopropyl, cyclobutyl, cyclopentyl, cyclohexyl, 1-methyl cyclopropyl, 1-methyl cyclobutyl, 1-methyl cyclopentyl and 1-methyl cyclohexyl. $R^1$ can also be an aryl or heteroaryl group, optionally substituted by halogen, $C_1$–$C_5$ alkoxy, di-$C_1$–$C_5$-alkylamino or $C_1$–$C_5$ alkyl. A particularly suitable aryl group is phenyl. Suitable heteroaryl groups are those which have 5 or 6 members and preferably contain an O, S or N atom. They can be anellated or condensed. Other optionally substituted aryl or heteroaryl groups include 2-methylphenyl, 3-methylphenyl, 4-methylphenyl, 2,4-dimethylphenyl, 2-fluorophenyl, 3-fluorophenyl, 4-fluorophenyl, 2-chlorophenyl, 3-chlorophenyl, 4-chlorophenyl, 2,4-dichlorophenyl, 3,4-dichlorophenyl, 3,5-dichlorophenyl, 2-methoxyphenyl, 3-methoxyphenyl, 4-methoxyphenyl, 3,4-dimethoxyphenyl, 3,4,5-trimethoxyphenyl, 2-furyl, 3-furyl, 5-bromo-2-methyl-3-furyl, 2-thienyl, 3-thienyl and 5-methyl-2-thienyl.

$NaNO_2$ is advantageously used as the alkali metal nitrite for the process of the invention. The preparation of the 3-$R^1$-3-oxo-1-aminopropane-1,1-diphosphonic acids of formula (IV) used as starting materials is described in German application 36 11 522 where $R^1$ is a tertiary alkyl group. Suitable starting materials for compounds of formula (IV) in which $R^1$ is an optionally substituted cyclopropyl group or an optionally substituted aryl group or heteroaryl group, are the 3-$R^1$-3-oxopropionic acid nitriles according to EP 0 089 011 which can be reacted by the method according to German application 36 11 522 to form compounds of formula (IV).

The reaction temperatures are preferably in the range of from 40° to 60° C., and more preferably in the range of from 45° to 55° C. In practice, the compound of formula (IV) is generally introduced first in suspension in dilute mineral acid, preferably hydrochloric acid, and the aqueous alkali metal nitrite solution subsequently added. The molar ratio of alkali metal nitrite to compound of formula (IV) is preferably in the range of from 3:1 to 5:1. The completion of the reaction may be verified by standard chromatographic methods.

The secondary product $R^1COOH$ and unreacted starting material of formula (IV) are then removed from the reaction mixture by extraction, excess nitrous acid is destroyed, for example with hydrazine, and the compound corresponding to general formula (III) is obtained as a salt by addition of a base. The reaction product corresponding to general formula (III) in which M represents H, can then be isolated therefrom by careful working up in known manner using an acidic reagent.

Suitable acidic reagents are mineral acids, such as hydrochloric acid, sulfuric acid, nitric acid, or phosphoric acid, organic acids and also acidic and strongly acidic ion exchange resins. Strongly acidic ion exchange resins are preferred.

The resulting reaction product corresponding to general formula (III), in which M represents H, is then optionally convetted by addition of basic reagents corresponding to the formula $M^+OH^-$, where $M^+$ is an alkali metal or ammonium cation, into its water-soluble salts, preferably its alkali metal salts and more preferably its sodium salts, and is isolated from the reaction mixture and purified by generally known methods, for example, by crystallizing out the reaction product dissolved in the reaction mixture at an elevated temperature by cooling or by precipitating the reaction product by addition of a solvent, separating the deposit obtained or the crystals from the dissolved reactants either by decanting off the mother liquor or by filtration, subsequently drying the deposit or the crystals, and optionally further purifying them by recrystallization.

In addition, it has surprisingly been found that the compounds of formula (III) show excellent complexing properties with respect to alkaline earth metal ions, particularly calcidum ions. This can readily be demonstrated, for example, by the so-called "Hampshire test".

Besides their excellent complexing power, the compounds of formula (III) are distinguished by strong threshold activity, i.e., they are capable of preventing the precipitation of poorly soluble alkaline earth metal salts, particularly alkaline earth metal carbonates, sulfates, phosphates and silicates, even in seeding quantities, i.e., substoichiometric quantities.

They can be widely used as complexing agents. For example, they can be specifically used for the processes involved in the softening of water, in which case the threshold effect mentioned above plays an important role. Accordingly, there is no need to use stoichiometric quantities; instead, calcite precipitation can be significantly retarded even with substiochiometric quantities.

They are also eminently suitable for use as corrosion and scale inhibitors for cooling waters, particularly in combination with additives known per se. They can also be used as complexing builders in detergents and cleaning preparations and can be used in combination with known anionic, cationic and nonionic wetting agents.

To this end, one or more compounds corresponding to formula (III), in which M is as defined above, is preferably used in a quantity of from 1 to 50 mg/l in compositions used as thresholders against calcite formation in aqueous solutions. Compositions containing one or more compounds corresponding to formula (III) in which M is an alkali metal cation, preferably a sodium ion, in concentrations of 5 to 50 mg/l, have been found to be particularly effective in this regard.

Compositions such as these are particularly suitable for preventing the deposition of calcite in aqueous solutions, e.g., cooling water, even at very high scale-forming concentrations. They need only be used in a comparatively low concentration for this purpose, which makes them distinctly superior to other structurally comparable complexing compositions.

The compounds of formula (III) are also useful for pharmaceutical purposes, for example, for the treatment of disorders affecting the calcium or phosphate metabolism and their associated illnesses. In addition, the hydroxyacetonitrile diphosphonic acid and its salts can be used in cosmetic preparations for oral hygiene, such as for example mouthwashes, tooth powders, tooth creams or tooth pastes; in dental fixatives, for the treatment of tartar and for the prophylaxis of tartar. It is known from German application 32 37 573 that organic triphosphonic acids or tetraphosphonic acids can be labeled with technetium-99m and then used for the scintigraphic display of RES-containing organs and the lymph vessels. Diphosphonic acid compounds, such as technetium-99m-1,1-diphosphonopropane-2,3-dicarboxylic acid, are also used for skeletal scintigraphy.

Finally, the compound according to the invention and its salts can be used as an intermediate product for organic syntheses.

The invention is illustrated by not limited by the following Examples.

EXAMPLES

Example 1

0.20 mol (63.4 g) 4-ethyl-4-methyl-3-oxo-1-aminohexane-1,1-di-phosphonic acid (IV) $R^2=R^3=CH_2CH_3$, $R^4=CH_3$) were suspended in 600 ml 2N hydrochloric acidd and a solution of 0.8 mol (55.2 g) sodium nitrite dissolved in 1104 ml water were added dropwise to the resulting suspension with stirring over a period of 7 hours at 50° C. 2-Ethyl-2-methyl-butyric acid was formed as the organic phase and was extracted with ether. Unused nitrous acid was removed with hydrazine before working up. The aqueous phase was concentrated to around 300 ml in a rotary evaporator and alkylized to pH 9 with sodium hydroxide. The tetrasodium salt of hydroxyacetonitrile diphosphonic acid (III, M=Na) crystallized out from the cold solution in the form of the octahydrate. The yield comprised 65% (58.4 g).

Elemental analysis in %:
Calculated: P 13.8 C 5.35 H 3.79 N 3.21 Na 20.5 $H_2O$ 32.1
Found: P 13.8 C 5.33 H 3.85 N 3.20 Na 19.9 $H_2O$ 32.2

Example 2

The calcium complexing power was determined by the Hampshire test in which the hydroxyacetonitrile diphosphonic acid, to which $Na_2CO_3$ has been added, was titrated with a 0.2 molar calcium chloride solution at pH 11 until it remained cloudy. Hydroxyacetonitrile diphosphonic acid was used in the form of its tetrasodium salt and the measured values obtained were converted for the pure diphosphonic acid.

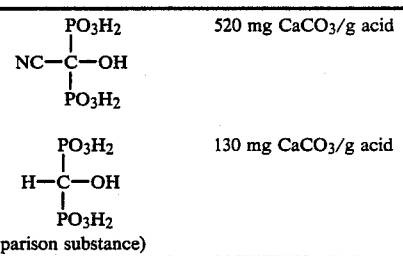

|  |  |
|---|---|
| PO3H2<br>\|<br>NC—C—OH<br>\|<br>PO3H2 | 520 mg CaCO3/g acid |
| PO3H2<br>\|<br>H—C—OH<br>\|<br>PO3H2<br>(as comparison substance) | 130 mg CaCO3/g acid |

Example 3

The precipitation-modifying properties, i.e. the ability of a complexing agent to prevent or retard the scaling of poorly soluble calcium salts, for example calcite, in substoichiometric quantities, was investigated in the substoichiometric range from 5 to 50 ppm. Hydroxyacetonitrile diphosphonic acid was used in the form of its tetrasodium salt and the measured values obtained were converted for the pure diphosphonic acid.

The determination was carried out by standard test method 03-74 of the National Association of Corrosion Engineers (NACE). Scale-forming conc.: 4000 mg $CaCO_3/l$

|  | 5 | 10 | 20 | 40 | 50 ppm |
|---|---|---|---|---|---|
| PO3H2<br>\|<br>NC—C—OH<br>\|<br>PO3H2 | 78 | 90 | 92 | 93 | 95 |

-continued

| | 5 | 10 | 20 | 40 | 50 ppm |
|---|---|---|---|---|---|
| H$_3$C—C(PO$_3$H$_2$)(PO$_3$H$_2$)—OH (as comparison substance) | 70 | 74 | 80 | 83 | 85 |

Example 4

A crucial step in the formation of tartar is the conversion of calcium hydrogen phosphate into hydroxyl apatite. As this Example shows, this process can be effectively prevented by the hydroxyacetonitrile diphosphonic acid of the invention. To this end, the degree of inhibition of this conversion was measured by determining the protons released in a calcium phosphate solution supersaturated at 60° C. in accordance with the following equation:

$$5\ CaHPO_4 + H_2O \longrightarrow Ca_5(OH)(PO_4)_3 + 2\ H_3PO_4$$

| Hydroxyacetonitrile diphosphonic acid | 91% inhibition |
|---|---|
| Hydroxymethane diphosphonic acid (as comparison substance) | 81% inhibition |

Example 5

The hydroxyacetonitrile diphosphonic acid of the invention effectively reduces the solubility of apatite by absorbing it on the tartar surface. To determine this property, the solubility of synthetic apatite after treatment with the hydroxyacetonitrile diphosphonic acid is determined by comparison with untreated apatite. To this end, a suspension of apatite is kept at pH 5 by neutralizing the hydroxyl ions passing into solution with lactic acid and determining the consumption of acid required for this purpose.

| | Reduction of the solubility of apatite |
|---|---|
|  | 65% |
| H$_3$C—C(PO$_3$H$_2$)(PO$_3$H$_2$)—OH (as comparison substance) | 53% |

We claim:

1. A compound which is hydroxyacetonitrile diphosphonic acid or a salt thereof of the formula

in which each M independently is H or an alkali metal cation or the ammonium cation R$^5$R$^6$R$^7$R$^8$N+ in which R$^5$, R$^6$, R$^7$ and R$^8$ independently of one another are hydrogen or a branched or unbranched C$_1$-C$_{12}$ alkyl radical.

2. The compound of claim 1 wherein each M is a cation of a water soluble base.

3. The compound of claim 1 wherein each M is an alkali metal cation.

4. The compound of claim 1 wherein each M is sodium.

5. The compound of claim 1 wherein each M is H.

6. The compound of claim 1 wherein each M is an ammonium cation of the formula R$^5$R$^6$R$^7$R$^8$N+, in which R$^5$, R$^6$, R$^7$ and R$^8$ independently of one another represent hydrogen or an unbranched or branched C$_1$-C$_{12}$ alkyl radical.

7. A process for the preparation of a hydroxyacetonitrile diphosphonic acid or salt thereof corresponding to the following general formula

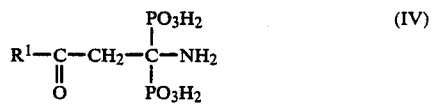

in which each M independently is H or an alkali metal cation or the ammonium cation R$^5$R$^6$R$^7$R$^8$N+ in which R$^5$, R$^6$, R$^7$ and R$^8$ independently of one another are hydrogen or a branched or unbranched C$_1$-C$_{12}$ alkyl radical, comprising the steps of A. reacting a 3-R$^2$-3-oxo-1-aminopropane-1,1-diphosphonic acid of the formula $$R^1-\underset{\underset{O}{\|}}{C}-CH_2-\underset{\underset{PO_3H_2}{|}}{\overset{\overset{PO_3H_2}{|}}{C}}-NH_2 \quad (IV)$$

in which R$^1$ represents
a tertiary alkyl group having the general formula —(R$^2$)C(R$^3$)(R$^4$), where R$^2$ and R$^3$ independently of one another represent a C$_1$-C$_3$ alkyl group, and R$^4$ is a C$_1$-C$_{10}$ alkyl group,
a cycloalkyl group which can be substituted by a methyl or ethyl group, or
an aryl or heteroaryl group which can be substituted by halogen, C$_1$-C$_5$ alkoxy, di-C$_1$-C$_5$ alkylamino or C$_1$-C$_5$ alkyl,
with nitrous acid, wherein the molar ratio of nitrous acid to the compound of formula IV being in the range of from about 1:1 to about 6:1, at a temperature of from about 20° to about 75° C. to form a reaction mixture containing a compound of formula III; and B. isolating the compound of formula III from the reaction mixture.

8. The process of claim 7 wherein the nitrous acid is generated in situ from an alkali metal nitrite and a dilute mineral acid.

9. The process of claim 8 wherein the alkali metal nitrite is sodium nitrite.

10. The process of claim 7 wherein the molar ratio of nitrous acid to the compound of formula IV is in the range of from about 3:1 to about 5:1.

11. The process of claim 7 wherein the reaction temperature is in the range of from about 40° to about 60° C.

12. The process of claim 11 wherein the reaction temperature is in the range of from about 45° to about 55° C.

13. A process for the preparation of a hydroxyacetonitrile diphosphonic acid or salt thereof corresponding to the following general formula

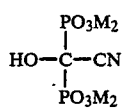

in which each M is H or an alkali metal cation or the ammonium cation $R^5R^6R^7R^8N^+$ in which $R^5$, $R^6$, $R^7$ and $R^8$ independently of one another are hydrogen or a branched or unbranched $C_1$–$C_{12}$ alkyl radical, comprising the steps of:

A. reacting a 3-$R^1$-3-oxo-1-aminopropane-1,1 diphosphonic acid or the formula

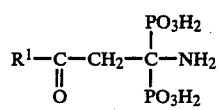

in which $R^1$ represents
a tertiary alkyl group having the general formula —$(R^2)C(R^3)(R^4)$, where $R^2$ and $R^3$ independently of one another represent a $C_1$–$C_3$ alkyl group, and $R^4$ is a $C_1$–$C_{10}$ alkyl group,
a cycloalkyl group which can be substituted by a methyl or ethyl group, or
an aryl or heteroaryl group which can be substituted by halogen, $C_1$–$C_5$ alkoxy, di-$C_1$–$C_5$-alkylamino or $C_1$–$C_5$ alkyl,
with nitrous acid prepared in situ from an alkali metal nitrite and a dilute mineral acid wherein the molar ratio of nitrous acid to the compound of formula IV being in the range of from about 1:1 to about 6:1, at a temperature of from about 20° C. to about 75° C. to form a reaction mixture containing a compound of formula III;

B. treating the reaction mixture with an acidic reagent to form a compound of formula III wherein all M groups are hydrogen; and, where the M groups of formula III are other than hydrogen, C. treating the compound of formula III where the M groups are hydrogen with a basic reagent of the formula $M^+OH$, where $M^+$ is an alkali metal or ammonium cation $R^5R^6R^7R^8N^+$, where $R^5$, $R^6$, $R^7$ and $R^8$ have the meaning given above, to form a compound of formula III in which M is an alkali metal or ammonium cation.

14. The process of claim 13 wherein in step A the molar ratio of nitrous acid to the compound of formula IV is in the range of from about 3:1 to about 5:1.

15. The process of claim 13 wherein in step A the reaction temperature is in the range of from about 40° to about 60° C.

16. The process of claim 15 wherein the step A the reaction temperature is in the range of from about 45° to about 55° C.

17. The process of claim 13 wherein in step B the acidic reagent is a mineral acid, an organic acid, or an acidic ion exchange resin.

18. The process of claim 17 wherein in step B the acidic reagent is an acidic ion exchange resin.

19. The process of claim 13 wherein in step C the basic reagent is NaOH.

20. A method of preventing or minimizing the precipitation of alkaline earth metal salts from aqueous solutions comprising adding thereto a complexing quantity of a compound of claim 1.

21. The method of claim 20 wherein the aqueous solution is cooling water.

22. The method of claim 20 wherein the compo9und of claim 1 is added in a quantity of from about 1 to about 50 mg/l of aqueous solution.

23. The method of claim 22 wherein from about 5 to about 50 mg/l is added, and in the compound of claim 1 M is an alkali metal cation.

* * * * *